(12) United States Patent
Kato

(10) Patent No.: US 10,067,057 B2
(45) Date of Patent: Sep. 4, 2018

(54) MEASUREMENT DEVICE, METHOD, AND RECORDING MEDIUM

(71) Applicant: ADVANTEST CORPORATION, Tokyo (JP)

(72) Inventor: Eiji Kato, Miyagi (JP)

(73) Assignee: ADVANTEST CORPORATION, Tokyo (JP)

( * ) Notice: Subject to any disclaimer, the term of this patent is extended or adjusted under 35 U.S.C. 154(b) by 267 days.

(21) Appl. No.: 13/860,034

(22) Filed: Apr. 10, 2013

(65) Prior Publication Data

US 2013/0284930 A1 Oct. 31, 2013

(30) Foreign Application Priority Data

Apr. 25, 2012 (JP) ................................. 2012-099444

(51) Int. Cl.
  *G01N 21/59* (2006.01)
  *G01N 3/40* (2006.01)
  (Continued)

(52) U.S. Cl.
  CPC ............... *G01N 21/59* (2013.01); *G01N 3/40* (2013.01); *G01N 15/088* (2013.01);
  (Continued)

(58) Field of Classification Search
  CPC .................................................. G01N 21/3581
  (Continued)

(56) References Cited

U.S. PATENT DOCUMENTS 4,314,210 A * 2/1982 Everett .................. H01S 3/083
   372/18
5,085,510 A * 2/1992 Mitchell .................... 356/237.1
(Continued)

FOREIGN PATENT DOCUMENTS

JP 05-142097 6/1993
JP 2008-076159 4/2008
(Continued)

OTHER PUBLICATIONS

M. Donoso et al., "Prediction of Tablet Hardness and Porosity Using Near-Infrared Diffuse Reflectance Spectroscopy as a Nondestructive Method," Pharmaceutical Development and Technology, vol. 8, No. 4, 2003, pp. 357-366.

(Continued)

*Primary Examiner* — Edwin Gunberg
(74) *Attorney, Agent, or Firm* — Greenblum & Bernstein, P.L.C.

(57) ABSTRACT

According to the present invention, a measurement device includes an electromagnetic wave detector, a phase measurement unit and a deriving unit. The electromagnetic wave detector detects an electromagnetic wave having a frequency equal to or more than 0.02 THz and equal to or less than 12 THz having traveled inside an object to be measured, which is an aggregation of particles. The phase measurement unit measures a change in phase of the electromagnetic wave generated by the travel inside the object to be measured based on a detection result by the electromagnetic wave detector. The deriving unit derives hardness or porosity of the object to be measured based on a measurement result by the phase measurement unit.

3 Claims, 5 Drawing Sheets

(51) Int. Cl.
  *G01N 15/08* (2006.01)
  *G01N 21/3581* (2014.01)
  *G01N 33/15* (2006.01)
  G01N 3/06 (2006.01)
  G01N 15/00 (2006.01)
  G01N 9/24 (2006.01)
  G01N 21/95 (2006.01)

(52) U.S. Cl.
  CPC ......... *G01N 21/3581* (2013.01); *G01N 33/15* (2013.01); *G01N 3/068* (2013.01); *G01N 9/24* (2013.01); *G01N 21/9508* (2013.01); *G01N 2015/0092* (2013.01); *G01N 2015/0846* (2013.01); *G01N 2203/0076* (2013.01)

(58) Field of Classification Search
  USPC ...................................................... 250/341.1
  See application file for complete search history.

(56) References Cited

U.S. PATENT DOCUMENTS

| 5,161,044 | A | * | 11/1992 | Nazarathy | H04B 1/62 398/194 |
|---|---|---|---|---|---|
| 5,303,033 | A | | 4/1994 | Matsuzaki | |
| 2009/0059205 | A1 | | 3/2009 | Itsuji | |
| 2009/0153838 | A1 | | 6/2009 | Vugts et al. | |
| 2009/0231571 | A1 | | 9/2009 | Itsuji | |
| 2010/0148070 | A1 | * | 6/2010 | Ho et al. | 250/341.8 |
| 2013/0125064 | A1 | | 5/2013 | Ebina et al. | |

FOREIGN PATENT DOCUMENTS

| JP | 2009-075069 | 4/2009 |
|---|---|---|
| WO | 2006/092557 | 9/2006 |
| WO | 2012/005005 | 1/2012 |

OTHER PUBLICATIONS

M. Hangyo et al., "Spectroscopy by pulsed terahertz radiation," Measurement Science and Technology, vol. 13, 2002, pp. 1727-1738.

T. Ervasti et al., "A Study on the Resolution of a Terahertz Spectrometer for the Assessment of the Porosity of Pharmaceutical Tablets," Applied Spectroscopy, vol. 66, No. 3, 2012, pp. 319-323.

L.A. Wall et al., "Use of terahertz time-domain spectroscopy to correlate refractive index and hardness for Avicel PH-101 tablets", Journal of Pharmacy and Pharmacology, vol. 62, No. 10, XP055164682 , Oct. 1, 2010, pp. 1485-1486.

Robert K May et al., "Pharmaceutical Tablet Hardness Measurements with THz Pulsed Imaging", Infrared, Millimeter, and Terahertz Waves, 2009. IRMMW-THZ 2009. 34$^{th}$ International Conference on, IEEE, Piscataway, NJ, USA, Sep. 21, 2009, XP031563195, pp. 1-2.

Juuti M et al., "Optical and terahertz measurement techniques for flat-faced pharmaceutical tablets: a case study of gloss, surface roughness and bulk properties of starch acetate tablets", Measurement Science and Technology, IOP, Bristol, GB, vol. 20, No. 1, XP020152543, Jan. 1, 2009, pp. 15301—(9pp).

Yao-Chun Shen, "Terahertz pulsed spectroscopy and imaging for pharmaceutical applications: A review", International Journal of Pharmaceutics, Elsevier BV, NL, vol. 417, No. 1, XP02828371, Jan. 6, 2011, pp. 48-60.

European Search report in European Patent Application No. 13165286.9, dated Feb. 5, 2015.

Office Action issued in Japan Counterpart Patent Appl. No. 2012-099444, dated Aug. 31, 2015.

Office Action issued in Japan Patent Appl. No. 2012-099444, dated Mar. 9, 2016.

* cited by examiner (a)

(b)

(a)

(b)

(a)

(b)

though it seemed like a mouthful, 

MEASUREMENT DEVICE, METHOD, AND RECORDING MEDIUM

BACKGROUND ART

1. Technical Field of the Invention

The present invention relates to measurement of hardness and porosity of an object to be measured (such as a tablet) which is an aggregation of particles.

2. Related Art

Hardness and porosity of a pharmaceutical preparation (tablet and preparation particles forming the tablet) forms important characteristics influencing efficiency of a medicine. In medicines, a solid preparation is manufactured by granulating, tableting, and coating a mixture of raw materials such as drug substance which is an effective component as well as an excipient, a binder, and a disintegrator.

Characteristics of the solid preparation are affected by a crystal form, an average particle diameter, and a granularity distribution of each of raw material. The characteristics of the solid preparation are also affected by conditions of a manufacturing process. The characteristics of the solid preparation are affected by a device scale (capacity), an agitating speed, a pressure, and a temperature for example in a granulation process. The characteristics of the solid preparation are affected by a tableting pressure in a tableting process, for example.

In this way, the characteristics of the solid preparation are affected in a complex way by various factors of the raw materials and the manufacturing process. Therefore, there is a difficulty in a logical estimation of the characteristics of the solid preparation. Thus, the quality of the solid preparation is guaranteed by an empirical design of a batch process and validation.

Meanwhile, according to the guideline of the International Conference on Harmonisation (ICH) of Japan, the United States, and the EU, it is required to sufficiently verify medicine quality risks on the stage of research and development, to acquire a large amount of data by monitoring critical quality attributes (CQAs) associated with the quality risks with high importance in the manufacturing process, and to understand the characteristics based on scientific basis. Then, the Quality by Design (QbD) which determines a design space based on these results and builds the quality in the process is proposed. Therefore, a development of the PAT (Process Analytical Technology) which enables monitoring and analysis of the CQA in real time and a nondestructive manner in the development of the medicine is expected.

The hardness and the porosity of the medical preparation are preparation attributes which can be CQAs. The measurement of the hardness is carried out by calculation of the density (density and hardness correlates with each other) by measurement of the weight and the volume and by a measurement of hardness through a destructive test with a tablet hardness tester. Moreover, the helium pycnometer and the mercury intrusion porosimetry are usually used to measure the porosity. However, both of these methods lack real time property, are destructive measurements, and are thus not suitable for PAT tool.

A nondestructive analysis by means of the near infrared (NIR) method for the tablet hardness and the porosity is proposed (refer to Non-patent Document 1).

It should be noted that Non-patent literature 2 describes how to calculate the complex amplitude transmittance.

PRIOR ART DOCUMENTS

[Non-patent Document 1] M. Donoso et al., "Prediction of Tablet Hardness and Porosity Using Near-Infrared Diffuse Reflectance Spectroscopy as a Nondestructive Method," PHARMACEUTICAL DEVELOPMENT AND TECHNOLOGY, Vol. 8, No. 4 (2003) pp. 357-366.

[Non-patent Document 2] M. Hangyo et al., Meas. Sci. Technol., Vol. 13 (2002) pp. 1727-1738

SUMMARY OF THE INVENTION

However, the technique described in Non-patent literature 1, which employs the diffused reflection method, provides information only on a surface layer in the case where a tablet is an object to be measured. Therefore, it is difficult to analyze the hardness and the porosity of the entire tablet.

The present invention has an object to measure hardness and porosity of an object to be measured (such as a tablet) which is an aggregation of particles.

According to the present invention, a measurement device includes: an electromagnetic wave detector that detects an electromagnetic wave having a frequency equal to or more than 0.02 THz and equal to or less than 12 THz having traveled inside an object to be measured, which is an aggregation of particles; a phase measurement unit that measures a change in phase of the electromagnetic wave generated by the travel inside the object to be measured based on a detection result by the electromagnetic wave detector; and a deriving unit that derives hardness or porosity of the object to be measured based on a measurement result by the phase measurement unit.

According to the thus constructed measurement device, an electromagnetic wave detector detects an electromagnetic wave having a frequency equal to or more than 0.02 THz and equal to or less than 12 THz having traveled inside an object to be measured, which is an aggregation of particles. A phase measurement unit measures a change in phase of the electromagnetic wave generated by the travel inside the object to be measured based on a detection result by the electromagnetic wave detector. A deriving unit derives hardness or porosity of the object to be measured based on a measurement result by the phase measurement unit.

According to the measurement device of the present invention, the deriving unit may derive the hardness or the porosity of the object to be measured based on a refractive index of the object to be measured derived based on the measurement result by the phase measurement unit.

According to the present invention, the measurement device may include a transport unit that transports the object to be measured into an area where the electromagnetic wave is irradiated, and transports the object to be measured out from the area.

According to the measurement device of the present invention, the transport unit may change a transport destination of the object to be measured depending on whether the derived hardness or porosity represents a value within a predetermined range or not.

According to the measurement device of the present invention, the object to be measured may be a tablet.

According to the measurement device of the present invention, the object to be measured may be particles stored in a container; and the electromagnetic wave may transmit through the container.

According to the measurement device of the present invention, the electromagnetic wave detector may detect the electromagnetic wave which has transmitted through the object to be measured.

According to the measurement device of the present invention, the object to be measured may be in contact with a reflection surface reflecting the electromagnetic wave; and the electromagnetic wave detector may detect the electromagnetic wave reflected by the reflection surface.

According to the measurement device of the present invention, the electromagnetic wave may have at least two types of frequency components.

According to the measurement device of the present invention, the phase measurement unit may measure a phase difference between the electromagnetic wave and an electromagnetic wave for reference which does not travel inside the object to be measured.

According to the present invention, the measurement device may include a thickness measurement unit that measures a thickness of the object to be measured.

The present invention is a measurement method with using a measurement device having an electromagnetic wave detector that detects an electromagnetic wave having a frequency equal to or more than 0.02 THz and equal to or less than 12 THz having traveled inside an object to be measured, which is an aggregation of particles, the method including: a phase measurement step that measures a change in phase of the electromagnetic wave generated by the travel inside the object to be measured based on a detection result by the electromagnetic wave detector; and a deriving step that derives hardness or porosity of the object to be measured based on a measurement result by the phase measurement step.

The present invention is a program of instructions for execution by a computer to perform a measurement process with using a measurement device having an electromagnetic wave detector that detects an electromagnetic wave having a frequency equal to or more than 0.02 THz and equal to or less than 12 THz having traveled inside an object to be measured, which is an aggregation of particles, the measurement process including: a phase measurement step that measures a change in phase of the electromagnetic wave generated by the travel inside the object to be measured based on a detection result by the electromagnetic wave detector; and a deriving step that derives hardness or porosity of the object to be measured based on a measurement result by the phase measurement step.

The present invention is a computer-readable medium having a program of instructions for execution by a computer to perform a measurement process with using a measurement device having an electromagnetic wave detector that detects an electromagnetic wave having a frequency equal to or more than 0.02 THz and equal to or less than 12 THz having traveled inside an object to be measured, which is an aggregation of particles, the measurement process including: a phase measurement step that measures a change in phase of the electromagnetic wave generated by the travel inside the object to be measured based on a detection result by the electromagnetic wave detector; and a deriving step that derives hardness or porosity of the object to be measured based on a measurement result by the phase measurement step.

MODES FOR CARRYING OUT THE INVENTION

A description will now be given of an embodiment of the present invention referring to drawings.

Figure 1:
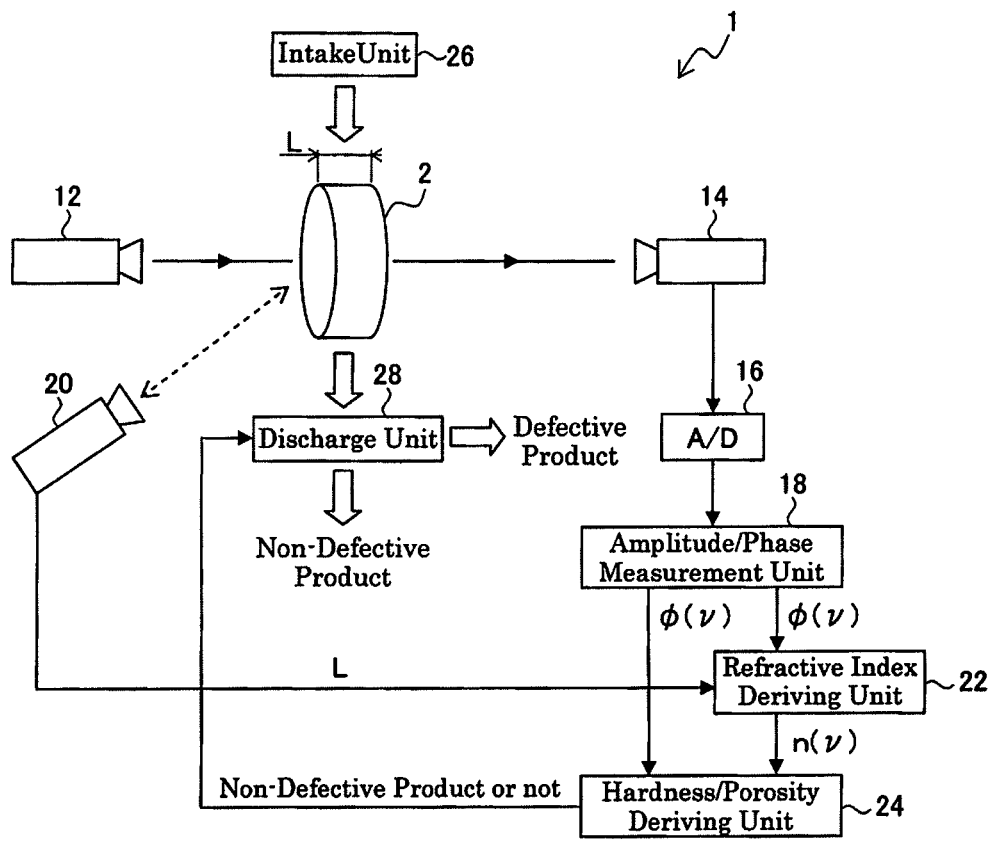
FIG. 1 is a diagram showing a configuration of a measurement device 1 according to an embodiment of the present invention.

FIG. 1 is a diagram showing a configuration of a measurement device 1 according to an embodiment of the present invention. The measurement device 1 is provided with an electromagnetic wave output device 12, an electromagnetic wave detector 14, an A/D converter 16, an amplitude/phase measurement unit 18, a length measurement device (thickness measurement unit) 20, a refractive index deriving unit 22, a hardness/porosity deriving unit 24, an intake unit 26, and a discharge unit 28.

The electromagnetic wave output unit 12 outputs a coherent electromagnetic wave to the tablet (object to be measured) 2. The electromagnetic wave may be in a pulse form or may be a continuous wave. It should be noted that the tablet 2 is an aggregation of particles and the thickness thereof is represented by L.

The frequency of the electromagnetic wave output from the electromagnetic wave output device 12 is equal to or higher than 0.02 THz and equal to or lower than 12 THz, and is preferably equal to or higher than 0.02 THz and equal to or lower than 3 THz, which represents excellent straight traveling property and transparency of the electromagnetic wave with respect to the tablet 2. It should be noted that the electromagnetic wave output from the electromagnetic wave output device 12 preferably has at least two types of frequency components.

The electromagnetic wave detector 14 detects the electromagnetic wave which has been output by the electromagnetic wave output device 12, and has traveled inside the tablet 2. In the example in FIG. 1, the electromagnetic wave detector 14 detects the electromagnetic wave which has been output by the electromagnetic wave output device 12, and has transmitted through the tablet 2. It should be noted that the frequency of the electromagnetic wave which has traveled inside the tablet 2 is the same as the frequency of the electromagnetic wave output from the electromagnetic wave output device 12.

The A/D converter 16 converts the electromagnetic wave detected by the electromagnetic wave detector 14 from an analog signal into a digital signal.

The amplitude/phase measurement unit 18 receives the detection result by the electromagnetic wave detector 14 via the A/D converter 16. The amplitude/phase measurement unit 18 measures a change $A(v)$ in the amplitude of the electromagnetic wave and a change $\phi(v)$ in the phase of the electromagnetic wave generated by the transmission inside the tablet 2 based on the detection result by the electromagnetic wave detector 14.

The change A(ν) in amplitude and the change φ(ν) in phase are represented by the complex amplitude transmittance T(ν).

$$T(v) = \frac{E_{sam}(v)}{E_{ref}(v)} = A(v)\exp(-i\phi(v)) \quad (1)$$

where $E_{sam}(v)$ is an electric field of the electromagnetic wave which has transmitted through the tablet 2. The amplitude/phase measurement unit 18 acquires $E_{sam}(v)$ from the detection result of the electromagnetic wave detector 14. It should be noted that ν is the frequency of the electromagnetic wave.

Moreover, $E_{ref}(v)$ is an electric field of a reference electromagnetic wave which does not travel inside the tablet 2. The electromagnetic wave detector 14 detects the electromagnetic wave output from the electromagnetic wave output device 12 in a state where the tablet 2 is removed from the measurement device 1. The amplitude/phase measurement unit 18 can receive a detection result via the A/D converter 16, thereby acquiring $E_{ref}(v)$.

The amplitude/phase measurement unit 18 divides $E_{sam}(v)$ by $E_{ref}(v)$, thereby obtaining the change A(ν) in amplitude and the change φ(ν) in phase. The change φ(ν) in phase is a phase difference between the electromagnetic wave which has transmitted through the tablet 2 and the reference electromagnetic wave which does not travel inside the tablet 2.

The length measurement device (thickness measurement unit) 20 is to measure the thickness L of the tablet 2 by means of a laser interferometry. It should be noted the length measurement device 20 may not use the laser interferometry as long as the length measurement device 20 can measure the thickness L of the tablet 2. For example, the length measurement device 20 may be a camera which can measure the size by means of image recognition.

The complex amplitude transmittance T(ν) can be represented by the following equation using a complex refractive index (=n(ν)+ik(ν)).

$$A(v)\exp(-i\phi(v)) \approx \frac{4n(v)}{(1+n(v))^2}\exp\left[\frac{i2\pi v(\tilde{n}(v)-1)L}{c}\right] \quad (2)$$

It should be noted that an imaginary part k(ν) (extinction coefficient) and a real part n(ν) of the complex refractive index are represented as follows.

$$\kappa(v) = \frac{c}{2\pi vL}\ln\left(\frac{4n(v)}{A(1+n(v))^2}\right) \quad (3)$$

$$n(v) = \frac{c\phi(v)}{2\pi vL} + 1 \quad (4)$$

where c denotes the light velocity.

It should be noted that an analytical sequential calculation method taking multiple reflections into consideration may be used for Equations (2), (3), and (4) (refer to M. Hangyo et al., Meas. Sci. Technol., Vol. 13 (2002) pp. 1727-1738).

Moreover, the imaginary part and the real part of the complex refractive index represented by Equations (3) and (4) can be obtained from an arbitrary single frequency according to Equation (2). However, the phase may change by 2π or more depending on the tablet 2 taking into consideration a realistic thickness (approximately 1 mm-10 mm) of the tablet 2 and the wavelength of the electromagnetic wave transmitting through the tablet 2, and thus the measurement is desirably carried out by using at least two frequencies within a range without phase change of 2π or more. Thus, as mentioned above, the electromagnetic wave output from the electromagnetic wave output device 12 has preferably two or more types of frequency components. For example, it is conceivable to consider a value obtained by averaging the refractive indices (refer to Equation (4)) measured for the respective frequency components as the refractive index of the tablet 2.

The refractive index deriving unit 22 receives the change φ(ν) in phase from the amplitude/phase measurement unit 18, and receives the thickness L of the tablet 2 from the length measurement device 20. Further, the refractive index deriving unit 22 assigns the change φ(ν) in phase and the thickness L to Equation (4) thereby deriving the refractive index n(ν) of the tablet 2.

The hardness/porosity deriving unit 24 receives the change φ(ν) in phase from the amplitude/phase measurement unit 18, or receives the refractive index n(ν) of the tablet 2 from the refractive index deriving unit 22. The hardness/porosity deriving unit 24 further derives the hardness or the porosity of the tablet 2 based on the change φ(ν) in phase (φ(ν) itself or the refractive index n(ν) of the tablet 2 derived by the refractive index deriving unit 22). It should be noted that the hardness/porosity deriving unit 24 may derive the hardness and the porosity of the tablet 2.

The change φ(ν) in phase and the refractive index n(ν) of the tablet 2 correlate with the hardness of the tablet 2. Thus, the regression models (PCR, PLS) can be built based on the change φ(ν) in phase and the refractive index n(ν) of the tablet 2 and the actual hardness of the tablet 2 actually measured by a tablet hardness tester or the like. The hardness of the tablet 2 can be derived from the change φ(ν) in phase or the refractive index n(ν) of the tablet 2 based on the regression model.

It should be noted that the refractive index n(ν) of the tablet 2 and the density of the tablet 2 are positively correlated with each other as described later. Moreover, the change φ(ν) in phase and the refractive index n(ν) of the tablet 2 correlate with each other as is apparent from Equation (4). Further, the density and the hardness of the tablet 2 correlate with each other (as the density increases, the hardness increases). The change φ(ν) in phase and the refractive index n(ν) of the tablet 2 correlate with the hardness of the tablet 2.

In order to investigate the correlation between the refractive index n(ν) and the density of the tablet 2, the tablets 2 using two types of drug substance (API-1 and API-2) were prepared. The tablets 2 had such a weight ratio that 94% of the drug substance, 5% of a polymer binder, and 1% of a lubricant (magnesium stearate) with respect to the total weight, and the same additives except APIs were used. Moreover, a force applied during the tableting was always 7 kN. Table 1 shows the produced tablets 2, and densities calculated from the weight and the size of the tablets 2. It is appreciated that the density of the tablet 2 using API-1 as drug substance is higher than that of the tablet 2 using API-2 as the drug substance, from Table 1.

TABLE 1

| API | No. | THICKNESS L (mm) | WEIGHT (mg) | DIAMETER (mm) | DENSITY (mg/mm$^3$) | REFRACTIVE INDEX |
|---|---|---|---|---|---|---|
| API-1 | 1 | 4.449 | 502 | 11.138 | 1.158 | 1.937 |
|  | 2 | 4.436 | 501 | 11.139 | 1.159 | 1.930 |
|  | 3 | 4.443 | 502 | 11.139 | 1.159 | 1.933 |
|  | 4 | 4.427 | 496 | 11.135 | 1.151 | 1.925 |
|  | 5 | 4.429 | 498 | 11.135 | 1.155 | 1.929 |
| API-2 | 6 | 4.720 | 505 | 11.148 | 1.096 | 1.619 |
|  | 7 | 4.717 | 501 | 11.146 | 1.089 | 1.616 |
|  | 8 | 4.712 | 501 | 11.145 | 1.090 | 1.616 |
|  | 9 | 4.713 | 502 | 11.146 | 1.092 | 1.615 |
|  | 10 | 4.716 | 503 | 11.146 | 1.093 | 1.618 |

Figure 2:
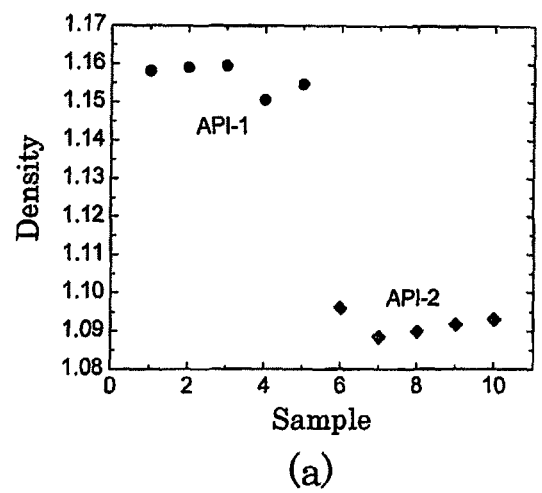
FIG. 2 includes a chart showing a plot (FIG. 2(a)) of the density calculated from the weight and the size of the tablets 2 produced by using the drug substances API-1 or API-2, and a chart showing a plot (FIG. 2(b)) of the refractive indices of the tablets 2 derived according to an embodiment of the present invention.
Figure 2:
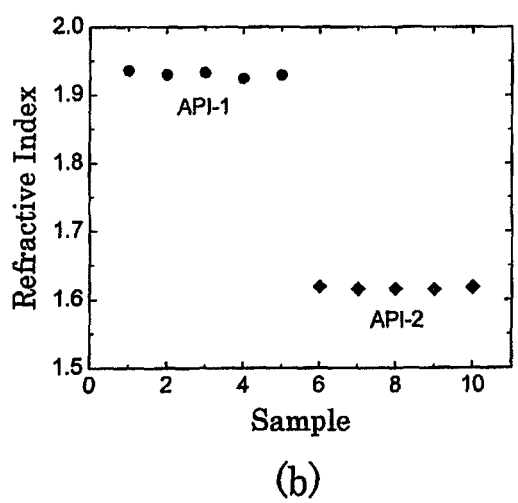

FIG. 2 includes a chart showing a plot (FIG. 2(a)) of the density calculated from the weight and the size of the tablets 2 produced by using the drug substances API-1 or API-2, and a chart showing a plot (FIG. 2(b)) of the refractive indices of the tablets 2 derived according to an embodiment of the present invention. A positive correlation is observed between the density and the refractive index of the tablets 2 from these plots (as the density increases, the refractive index increases).

The change φ(v) in phase and the refractive index n(v) of the tablet 2 correlate with the porosity of the tablet 2. Thus, regression models (PCR, PLS) can be built based on the change φ(v) in phase and the refractive index n(v) of the tablet 2 and the actual porosity of the tablet 2 actually measured by the mercury intrusion porosimetry or the like. The porosity of the tablet 2 can be derived from the change φ(v) in phase and the refractive index n(v) of the tablet 2 based on the regression model.

It should be noted that the refractive index n(v) of the tablet 2 and the porosity of the tablet 2 are positively correlated experimentally as described later. Moreover, the change φ(v) in phase and the refractive index n(v) of the tablet 2 correlate with each other as is apparent from Equation (4). Thus, the change φ(v) in phase and the refractive index n(v) of the tablet 2 correlate with the porosity of the tablet 2.

Eleven tablets of the tablet 2 using API-1 as drug substance were prepared, and five of them were stored at a humidity of 20% at the normal temperature (the same tablets 2 as in Table 1). The remaining six tablets were stored at a humidity of 90% at the normal temperature for 72 hours and then were stored at a humidity of 20% at the normal temperature. Sizes and weights of these eleven tablets 2 after the storage, and densities calculated therefrom are shown in Table 2.

Figure 3:
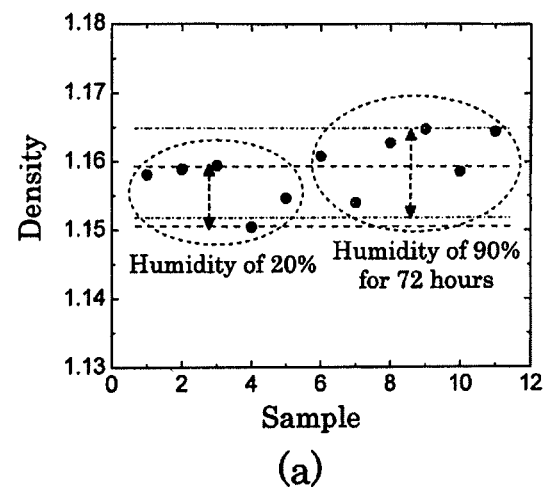
FIG. 3 includes a chart showing a plot (FIG. 3(a)) of the density calculated from the weight and the size of the tablets 2 stored at the different humidities, and a chart showing a plot (FIG. 3(b)) of the refractive indices of the tablets 2 derived according to an embodiment of the present invention.
Figure 3:
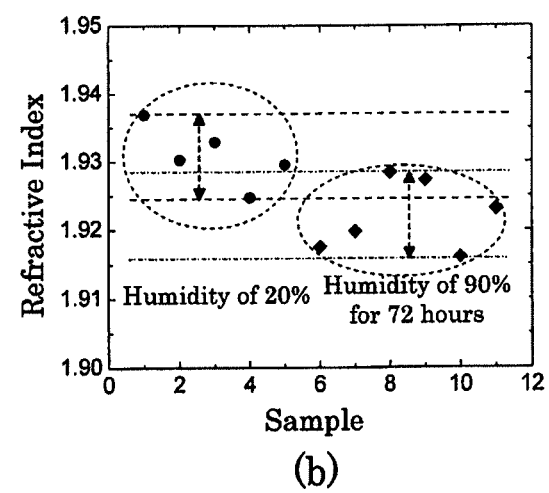

FIG. 3 includes a chart showing a plot (FIG. 3(a)) of the density calculated from the weight and the size of the tablets 2 stored at the different humidities, and a chart showing a plot (FIG. 3(b)) of the refractive indices of the tablets 2 derived according to an embodiment of the present invention. The t-test was applied to the density data calculated from the weights and the sizes, and a significant difference was not observed due to the difference in the storage conditions (refer to FIG. 3(a)). Meanwhile, the t-test was applied to the data on the refractive indices of the tablets 2 derived according to an embodiment of the present invention, a significant difference was observed due to the storage conditions, and it was found that the refractive indices of the samples stored at higher humidity are slightly lower (FIG. 3(b)). Further, the porosities were evaluated by the mercury intrusion porosimetry, and a result is obtained that the porosities are slightly lower for the tablets 2 stored at higher humidity. As a result, it was observed that the refractive index and the porosity of the tablet 2 derived according to an embodiment of the present invention positively correlate with each other (as the refractive index decreases, the porosity decreases).

The refractive index of the tablet 2 derived according to an embodiment of the present invention is a parameter representing an optical density of the tablet 2, and the refractive index increases as a ratio occupied by the air decreases in the tablets 2 having the same volume. Meanwhile, it seems that as the ratio occupied by the air increases in the tablet 2, the refractive index decreases. Thus, it seems that the change in refractive index derived according to an embodiment of the present invention is caused by the change in the porosity of the tablets 2 stored at the high humidity.

It should be noted that the hardness/porosity deriving unit 24 determines whether the derived hardness or the porosity of the tablet 2 is a value within a predetermined range or not, and provides the discharge unit 28 with a determination

TABLE 2

| API | STORAGE STATE | No. | THICKNESS L (mm) | WEIGHT (mg) | DIAMETER (mm) | DENSITY (mg/mm$^3$) | REFRACTIVE INDEX |
|---|---|---|---|---|---|---|---|
| API-1 | HUMIDITY: 20% | 1 | 4.449 | 502 | 11.138 | 1.158 | 1.937 |
|  |  | 2 | 4.436 | 501 | 11.139 | 1.159 | 1.930 |
|  |  | 3 | 4.443 | 502 | 11.139 | 1.159 | 1.933 |
|  |  | 4 | 4.427 | 496 | 11.135 | 1.151 | 1.925 |
|  |  | 5 | 4.429 | 498 | 11.135 | 1.155 | 1.929 |
|  | HUMIDITY 90% FOR 72 HOURS | 1 | 4.441 | 502 | 11.135 | 1.161 | 1.918 |
|  |  | 2 | 4.430 | 497 | 11.126 | 1.154 | 1.920 |
|  |  | 3 | 4.448 | 503 | 11.128 | 1.163 | 1.928 |
|  |  | 4 | 4.449 | 504 | 11.128 | 1.165 | 1.927 |
|  |  | 5 | 4.430 | 499 | 11.126 | 1.159 | 1.916 |
|  |  | 6 | 4.452 | 504 | 11.126 | 1.164 | 1.923 | result. For example, if the hardness of the tablet 2 exceeds a predetermined threshold, it is determined that the tablet 2 is a non-defective product, and otherwise it is determined that the tablet 2 is a defective product. For example, if the porosity of the tablet 2 is less than a predetermined threshold, the tablet 2 is determined as a non-defective product, and otherwise the tablet 2 is determined as a defective product.

The intake unit 26 and the discharge unit 28 form a transport unit for transporting the tablet 2 into an area where the electromagnetic wave is irradiated, and transporting the tablet 2 out from the area.

The intake unit 26 transports the tablet 2 into the area where the electromagnetic wave is irradiated. The discharge unit 28 transports the tablet 2 out from the area where the electromagnetic wave is irradiated.

The discharge unit 28 of the transport unit changes a destination of transport of the tablet 2 depending on whether the hardness/porosity deriving unit 24 has determined that the tablet 2 is a non-defective product or the tablet 2 is a defective product. For example, the tablet 2 determined as defective may be disposed.

A description will now be given of an operation of an embodiment of the present invention.

The electromagnetic wave output unit 12 outputs a coherent electromagnetic wave to the tablet (object to be measured) 2 brought in by the intake unit 26. The electromagnetic wave which has transmitted through the tablet 2 is detected by the electromagnetic wave detector 14. The detection result is converted into a digital signal by the A/D converter 16, and is fed to the amplitude/phase measurement unit 18. The amplitude/phase measurement unit 18 acquires the electric field $E_{sam}(v)$ of the electromagnetic wave which has transmitted through the tablet 2.

Moreover, the electromagnetic wave detector 14 detects the electromagnetic wave output from the electromagnetic wave output device 12 even in a state where the tablet 2 is removed from the measurement device 1. The amplitude/phase measurement unit 18 can receive the detection result via the A/D converter 16, thereby acquiring the electric field $E_{ref}(v)$ of the electromagnetic wave for reference.

The amplitude/phase measurement unit 18 divides $E_{sam}(v)$ by $E_{ref}(v)$, thereby obtaining the change $A(v)$ in amplitude and the change $\phi(v)$ in phase. The change $\phi(v)$ in phase is fed to the hardness/porosity deriving unit 24 or to the refractive index deriving unit 22.

The measurement unit (thickness measurement unit) 20 measures the thickness L of the tablet 2. The refractive index deriving unit 22 derives the refractive index $n(v)$ of the tablet 2 based on the thickness L of the tablet 2 and the change $\phi(v)$ in phase (refer to Equation (4)). The refractive index $n(v)$ of the tablet 2 is fed to the hardness/porosity deriving unit 24.

The hardness/porosity deriving unit 24 derives the hardness or the porosity of the tablet 2 by means of the regression models (PCR, PLS) based on the change $\phi(v)$ in phase or the refractive index $n(v)$ of the tablet 2. Further, the hardness/porosity deriving unit 24 determines whether the tablet 2 is a non-defective product or a defective product depending on whether the hardness or the porosity of the tablet 2 has a value within a predetermined range.

The discharge unit 28 of the transport unit changes the destination of transport of the tablet 2 depending on whether the hardness/porosity deriving unit 24 has determined that the tablet 2 is a non-defective product or the tablet 2 is a defective product. For example, the tablet 2 determined as defective may be disposed.

According to an embodiment of the present invention, the hardness or the porosity of an object to be measured which is an aggregation of particles (such as the tablet 2) can be measured.

Although the object to be measured is the tablet 2 according to an embodiment of the present invention, the object to be measured is not limited to the tablet as long as it is an aggregation of particles.

Figure 4:
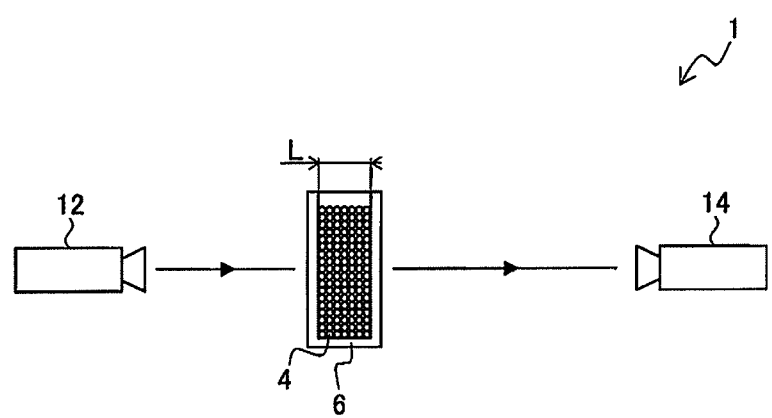
FIG. 4 is a diagram showing a configuration of the measurement device 1 in a case where the object to be measured is particles 4 stored in a container 6 according to an embodiment of the present invention.

FIG. 4 is a diagram showing a configuration of the measurement device 1 in a case where the object to be measured is particles 4 stored in a container 6 according to an embodiment of the present invention. It should be noted that only the electromagnetic wave output device 12, the electromagnetic wave detector 14, the container 6, and the particles 4 in the measurement device 1 are shown, and other components are not shown in FIG. 4.

The object to be measured is the particles 4 stored in the container 6, and the electromagnetic wave output from the electromagnetic wave output device 12 transmits through the container 6.

Moreover, the electromagnetic wave detector 14 detects the electromagnetic wave which has been output from the electromagnetic wave output device 12, and has transmitted through the tablet 2 according to an embodiment of the present invention. However, the electromagnetic wave detector 14 only needs to be capable of detecting the electromagnetic wave which was output by the electromagnetic wave output device 12, and has traveled inside the tablet 2 or the particles 4.

Figure 5:
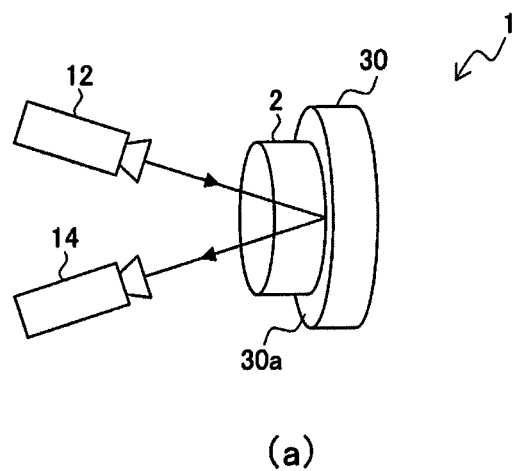
FIG. 5 includes a configuration (FIG. 5(a)) of the measurement device 1 in a case where the tablet 2 is in contact with a reflection surface 30a, and a configuration (FIG. 5(b)) of the measurement device 1 in a case where the particles 4 are in contact with the reflection surface 30a according to an embodiment of the present invention.
Figure 5:
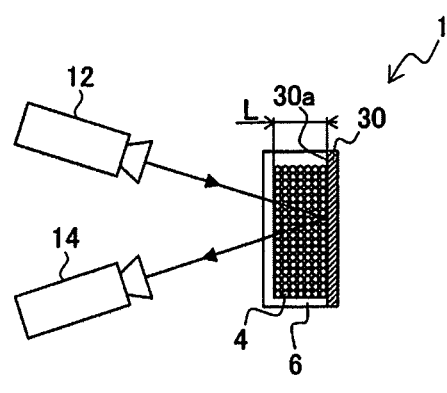

FIG. 5 includes a configuration (FIG. 5(a)) of the measurement device 1 in a case where the tablet 2 is in contact with a reflection surface 30a, and a configuration (FIG. 5(b)) of the measurement device 1 in a case where the particles 4 are in contact with the reflection surface 30a according to an embodiment of the present invention. It should be noted that only the electromagnetic wave output device 12, the electromagnetic wave detector 14, the container 6, and the particles 4 in the measurement device 1 are shown, and other components are not shown in FIG. 5.

Referring to FIG. 5(a), the tablet (object to be measured) 2 is in contact with the reflection surface 30a which reflects the electromagnetic wave. The reflection surface 30a is a bottom surface of a conductor 30 in a cylindrical shape (such as a die of a tableting machine). The electromagnetic wave output from the electromagnetic wave output device 12 travels inside the tablet 2, is reflected by the reflection surface 30a, travels inside the tablet 2 again, transmits through the tablet 2, and is detected by the electromagnetic wave detector 14.

In the case where the conductor 30 is used as die for the tableting machine, the electromagnetic wave output device 12 and the electromagnetic wave detector 14 can be built into the tableting machine, thereby monitoring in-line the hardness and the porosity of the tablet 2 during the manufacturing process.

Referring to FIG. 5(b), the particles (object to be measured) 4 are in contact with the reflection surface 30a which reflects the electromagnetic wave. The reflection surface 30a is a certain surface of the conductor 30. The electromagnetic wave output from the electromagnetic wave output device 12 travels inside the particles 4, is reflected by the reflection surface 30a, travels inside the particles 4 again, transmits through the particles 4, and is detected by the electromagnetic wave detector 14.

Moreover, the above-described embodiment may also be realized in the following manner. A computer having a CPU, a hard disk, and a media (such as a floppy disk (registered trade mark) and a CD-ROM) reader, and the media reader may be caused to read a medium recording a program realizing the above-described respective components such as the amplitude/phase measurement unit 18, the refractive index deriving unit 22, and the hardness/porosity deriving unit 24, thereby installing the program on the hard disk. This method may also realize the above-described functions.

The invention claimed is:

1. A measurement device comprising:
   an electromagnetic wave detector that detects an electromagnetic wave having a frequency equal to or more than 0.02 THz and equal to or less than 12 THz having traveled inside an object to be measured, which is an aggregation of particles;
   a phase measurer that measures a change in phase of the electromagnetic wave generated by the travel inside the object to be measured based on a detection result by the electromagnetic wave detector;
   a deriver that derives hardness or porosity of the object to be measured based on a measurement result itself by the phase measurer, said measurement result is a result itself and not a refractive index of the object to be measured; and
   a thickness measurer that measures a thickness of the object to be measured.

2. A measurement method with using a measurement device having an electromagnetic wave detector that detects an electromagnetic wave having a frequency equal to or more than 0.02 THz and equal to or less than 12 THz having traveled inside an object to be measured, which is an aggregation of particles, the method comprising:
   measuring a change in phase of the electromagnetic wave generated by the travel inside the object to be measured based on a detection result by the electromagnetic wave detector;
   deriving hardness or porosity of the object to be measured based on a measurement result itself by the measuring, said measurement result is a result itself and not a refractive index of the object to be measured; and
   measuring, via a thickness measurer, a thickness of the object to be measured.

3. A computer-readable medium having a program of instructions for execution by a computer to perform a measurement process using a measurement device having an electromagnetic wave detector that detects an electromagnetic wave having a frequency equal to or more than 0.02 THz and equal to or less than 12 THz having traveled inside an object to be measured, which is an aggregation of particles, the measurement process comprising:
   measuring a change in phase of the electromagnetic wave generated by the travel inside the object to be measured based on a detection result by the electromagnetic wave detector;
   deriving hardness or porosity of the object to be measured based on a measurement result itself by the measuring, said measurement result is a result itself and not a refractive index of the object to be measured; and
   measuring, via a thickness measurer, a thickness of the object to be measured.

* * * * *